United States Patent
Winkley et al.

(10) Patent No.: US 7,276,611 B2
(45) Date of Patent: Oct. 2, 2007

(54) PROCESS FOR SYNTHESIZING BETA-LACTAMASE INHIBITOR INTERMEDIATES

(75) Inventors: Michael William Winkley, Campbell Hall, NY (US); Anita Wai-Yin Chan, Ft. Lee, NJ (US); Ivo L. Jirkovsky, Waitsfield, VT (US); Kenneth Alfred Martin Kremer, Lawrenceville, NJ (US); Joseph Zeldis, New City, NY (US); Antonia Aristotelevna Nikitenko, Tarrytown, NY (US); Henry Lee Strong, Somerset, NJ (US); Tarek Mansour, New City, NY (US); Gulnaz Khafizova, West Nyack, NY (US); Aranapakam M. Venkatesan, Rego Park, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 356 days.

(21) Appl. No.: 10/844,243

(22) Filed: May 12, 2004

(65) Prior Publication Data

US 2004/0242874 A1 Dec. 2, 2004

Related U.S. Application Data

(60) Provisional application No. 60/471,458, filed on May 16, 2003.

(51) Int. Cl.
*C07D 231/54* (2006.01)
(52) U.S. Cl. ............ 548/360.1; 548/148; 548/217
(58) Field of Classification Search ......... 548/360.1, 548/148, 217; 544/73
See application file for complete search history.

(56) References Cited

U.S. PATENT DOCUMENTS

2004/0229324 A1* 11/2004 Matur et al. ............ 435/119

FOREIGN PATENT DOCUMENTS

GB 2118181 A 10/1983

OTHER PUBLICATIONS

Inanaga, et al.; Bull Chem. Soc. Jpn., vol. 52; p. 1989; 1979.
Ranganathan, D., et al.; "A Novel Proline Meso-Ionic Synthon"; Tetrahedron Letts.; vol. 24, No. 10; pp. 1067-1070; 1983.
Ranganathan, D., et al.; Indian J. Chem., 30B, 169-175 (1991).
Coleman, K.; Expert Opin. Invest. Drugs; vol. 4; p. 693; 1995.
Bush, K., et al.; Antimicrob. Agents Chemother.; vol. 39; p. 1211; 1995.
Sutherland, R.; Infection; vol. 23, No.4; pp. 191; 1995.
Breithaupt, H.; Nat. Biotechnol.; vol. 17, No. 12; pp. 1165-1169; 1999.
Bush, Karen; Current Pharmaceutical Design; vol. 5; pp. 839-845; 1999.
Payne, D.J., et al.; Exp. Opin. Invest Drugs; p. 247; 2000.
Jung No Lee, et al., Bull. Korean Chem. Soc., vol. 21, No. 8, pp. 761-762, 2000.
International Search Report PCT/US2004/014834.

* cited by examiner

*Primary Examiner*—Joseph K. McKane
*Assistant Examiner*—Rei-tsang Shiao
(74) *Attorney, Agent, or Firm*—Daniel B. Moran

(57) ABSTRACT

There is provided a process for the preparation of bicyclicheteroaryl carboxaldehydes having the structural Formula I where X and Y are defined in the specification

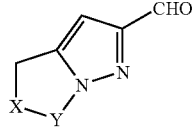

Formula I The bicyclic heteroaryl carboxaldehydes are useful as intermediates in the preparation of β-lactamase inhibitors.

19 Claims, No Drawings

PROCESS FOR SYNTHESIZING BETA-LACTAMASE INHIBITOR INTERMEDIATES

"This application claims priority from copending provisional Application No. 60/471,458 filed May 16, 2003 the entire disclosure of which is hereby incorporated by reference"

FIELD OF THE INVENTION

The invention relates to a process for synthesizing intermediate bicyclic heteroaryl carboxaldehydes useful in the synthesis of β-lactamase inhibitors which are useful in antibiotic therapy.

BACKGROUND OF THE INVENTION

New improved antibiotics are continually in demand, for the treatment of diseases in man. According to the World Health Organization, more than 95% of the *Staphylococcus aureus* isolates worldwide are now resistant to penicillin and up to 60% are resistant to methicillin (Breithaupt, H. *Nat. Biotechnol.* 17(12), 1165-9 (1999) and the references therein). Resistance is spreading from hospital-acquired infections to community-acquired pathogens, such as pneumococci and tuberculosis.

Penicillins and cephalosporins are the most frequently and widely used β-lactam antibiotics in the clinic. However, the development of resistance to β-lactam antibiotics by different pathogens has had a damaging effect on maintaining the effective treatment of bacterial infections. (Coleman, K. *Expert Opin. Invest. Drugs* 1995, 4, 693; Sutherland, R. *Infection* 1995, 23 (4) 191; Bush, K, *Cur. Pharm. Design* 1999, 5, 839-845) The most significant known mechanism related to the development of bacterial resistance to the β-lactam antibiotics is the production of class-A, class-B and class-C serine β-lactamases. These enzymes degrade the β-lactam antibiotics, resulting in the loss of antibacterial activity. Class-A enzymes preferentially hydrolyze penicillins where as Class-C lactamases have a substrate profile favoring cephalosporin hydrolysis. (Bush, K.; Jacoby, G. A.; Medeiros, A. A. *Antimicrob. Agents Chemother.* 1995, 39, 1211). To date over 250 different β-lactamases have been reported (Payne, D. J,: Du, W and Bateson, J. H. *Exp. Opin. Invest. Drugs* 2000, 247.) and there is a need for a new generation of broad spectrum β-lactamase inhibitors. Bacterial resistance to these antibiotics could be greatly reduced by administering the β-lactam antibiotic in combination with a compound which inhibits these enzymes. Accordingly, there is an ongoing need to discover new methods for the preparation of β-lactamase inhibitors.

The present invention satisfies the need for new processes for the preparation of β-lactamase inhibitors wherein said processes also provide advantages.

SUMMARY OF THE INVENTION

The present invention provides a new process for the preparation of intermediate bicyclic heteroaryl carboxaldehydes, of Formula I, useful for the synthesis of bicyclic heteroaryl substituted 6-alkylidene penems,

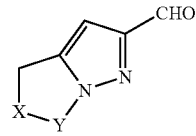

wherein:
Y is $(CH_2)_n$;
n is 1 or 2;
X is NR, O, S, or $CH_2$;
R is alkyl of 1 to 6 carbon atoms, or arylalkyl($C_1$ to $C_6$);
provided n is 2 when X is NR or O.

Alkyl is straight or branched chain alkyl moieties of 1 to 6 carbon atoms.

Arylalkyl($C_1$ to $C_6$) means an alkyl moiety of 1 to 6 carbon atoms substituted with an aryl moiety wherein the aryl moiety is defined as an aromatic hydrocarbon moiety having 6 to 12 carbon atoms and selected from the group: phenyl, α-naphthyl, β-naphthyl, biphenyl, anthryl, tetrahydronaphthyl, fluorenyl, indanyl, biphenylenyl, and acenaphthenyl. Arylalkyl($C_1$ to $C_6$) moieties include benzyl, 1-phenylethyl, 2-phenylethyl, 3-phenylethyl, 2-phenylpropyl, 4-nitrobenzyl and the like.

Bicyclic 6-alkylidene-penems are useful as betalactamase inhibitors. Bicyclic heteroaryl carboxaldehydes are key intermediates in the preparation of bicyclic heteroaryl substituted 6-alkylidene penems which have β-lactamase inhibitory and antibacterial properties and which includes (5R,6Z)-6-(5,6-dihydro-4H-pyrrolo[1,2-b]pyrazol-2-yl-methylene)-7-oxo-4-thiazabicyclo-[3.2.0]hept-2-ene-2-carboxylic acid, sodium salt.

In particular, key intermediates in the preparation of bicyclic heteroaryl carboxaldehydes as described herein are bicyclic heteroaryl-2-carboxylic acids which are advantageously selectively synthesized from a mixture of ester isomers by aqueous base hydrolysis of the desired ester and isolation of the resultant carboxylic acid product as the potassium salt.

An earlier patent application describes the preparation of bicyclic heteroaryl-2-carboxyaldehydes from a mixture of positional esters via chromatographic separation, reduction of the appropriate ester to the alcohol, and oxidation of the alcohol to the aldehyde (see U.S. Ser. No. 60/377052, filed May 1, 2002, Wyeth Case AM100862L1). The synthesis described herein eliminates the need for chromatography.

The present invention solves the problems of the existing methods and provides a method for the preparation of bicyclic heteroaryl carboxaldehydes of Formula I.

In this disclosure a number of terms are used and the following definitions are provided.

Aryl, as used herein refers to an aromatic hydrocarbon moiety of 6-12 carbon atoms and selected from the group: phenyl, α-naphthyl, β-naphthyl, biphenyl, anthryl, tetrahydronaphthyl, fluorenyl, indanyl, biphenylenyl, and acenaphthenyl.

As used herein, the term, $C_5$-$C_6$ cycloalkyl refers to a monocyclic saturated ring having 5 to 6 carbon atoms. Exemplary cycloalkyl rings include cyclopentyl, or cyclohexyl.

As used herein, the pharmaceutically acceptable salts of the basic compounds prepared the processes of this invention are those derived from such organic and inorganic acids as: lactic, citric, acetic, tartaric, fumaric, succinic, maleic, malonic, hydrochloric, hydrobromic, phosphoric, nitric, sulfuric, methanesulfonic, and similarly known acceptable acids. Where a carboxyl group is present, salts of the compounds prepared by the processes of this invention may be formed with bases such as alkali metals (Na, K, Li) or alkaline earth metals (Ca or Mg).

As used herein, mineral acids mean sulfuric acid, hydrochloric acid and the like.

As used herein, the term "reacting" is intended to represent bringing the chemical reactants together under conditions such to cause the chemical reaction indicated to take place.

The term "leaving group" generally refers to groups readily displaceable by a nucleophile, such as an amine. Such leaving groups are well known in the art. Examples of such leaving groups include, but are not limited to, N-hydroxysuccinimide, N-hydroxybenzotriazole, fluorine, chlorine, bromine, 1,1'-carbonyldiimidazole and the like.

In particular this invention provides a process for the preparation of bicyclic heteroaryl carboxaldehydes of Formula I

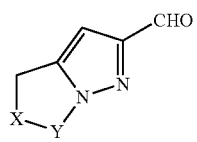

wherein:
Y is $(CH_2)_n$;
n is 1 or 2;
X is NR, O, S, or $CH_2$;
R is alkyl of 1 to 6 carbon atoms, or arylalkyl($C_1$ to $C_6$);
provided n is 2 when X is NR or O;

which process comprises the steps of:
a. nitrosating an amino acid 1 of the formula

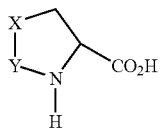

wherein X and Y are defined as above with a nitrosating reagent to form a nitroso compound of formula 2 wherein X and Y are defined as above

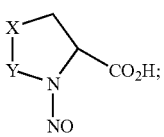

b. reacting the nitroso compound 2 with a dehydrating agent and neutralizing with inorganic base to form the ylide of formula 3 wherein X and Y are defined as above

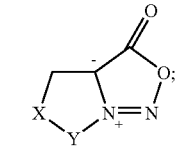

c. reacting the ylide of formula 3 with a propiolate ester of formula 4

$$HC{\equiv}CCO_2R_1 \qquad 4$$

where $R_1$ is alkyl of 1 to 6 carbon atoms, in aprotic solvents to form a mixture of bicyclic-heteroaryl-3-carboxylate ester 5 and bicyclic-heteroaryl-2-carboxylate ester 6 wherein $R_1$, X and Y are defined as above

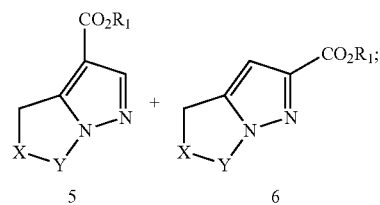

d. reacting the mixture of bicyclic-heteroaryl 3-carboxylate ester 5 and bicyclic-heteroaryl-2-carboxylate ester 6 with a hydrolyzing reagent $MOR_5$ where M is an alkali metal or $R_4N$ where $R_4$ is straight or branched alkyl of 1 to 6 carbon atoms when $R_5$ is H, in an alcohol solvent, or when M is an alkali metal and $R_5$ is alkyl of 1 to 6 carbon atoms in an aqueous alcohol solvent to preferentially form a salt 7 of the formula wherein X, Y and M are defined as above

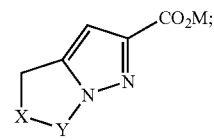

e. isolating the salt 7;
f. reacting the salt 7 with acid to form bicyclic-heteroaryl-2-carboxylic acid 8 where X and Y are defined as above

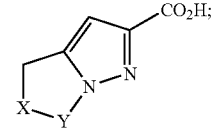

g. reacting the bicyclic-heteroaryl-2-carboxylic acid 8 or salts thereof with an acid halide reagent or coupling reagent to form an activated intermediate 9 where Q is a leaving group formed from the coupling reagent or acid halide reagent and wherein X and Y are defined as above

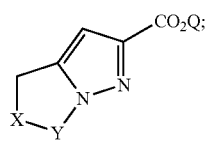

9 h. reacting an activated intermediate 9 or the bicyclic-heteroaryl-2-carboxylic acid 8 with a substituted hydroxylamine of the formula $R_3NHOR_2$ 10 where $R_2$ and $R_3$ are independently alkyl of 1 to 6 carbon atoms in the presence of an organic base or inorganic base to provide an amide of formula 11 wherein X, Y, $R_2$ and $R_3$ are defined as above

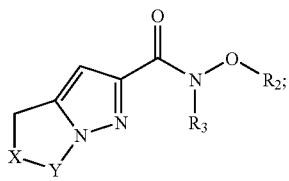

11 i. reducing the amide 11 with a reducing agent to provide a bicyclic heteroaryl carboxaldehyde of Formula I wherein X and Y are defined as above

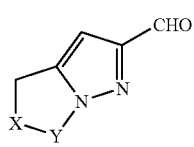

I and isolating the heteroaryl carboxaldehyde of Formula I.

A further embodiment of this invention provides a process for the preparation of bicyclic heteroaryl carboxaldehydes of Formula I

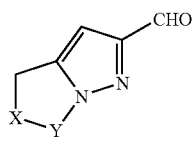

I wherein:
Y is $(CH_2)_n$;
n is 1 or 2;
X is NR, O, S, or $CH_2$;
R is alkyl of 1 to 6 carbon atoms, or arylalkyl($C_1$ to $C_6$);
provided n is 2 when X is NR or O;

which process comprises the steps of:

a. reacting a mixture of bicyclic-heteroaryl-3-carboxylate ester 5 and bicyclic-heteroaryl-2-carboxylate ester 6 wherein $R_1$ is alkyl of 1 to 6 carbon atoms and X and Y are defined as above

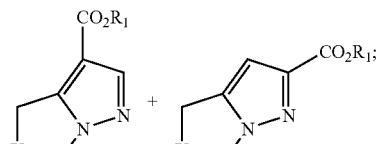

5       6 with a hydrolyzing reagent $MOR_5$ where M is an alkali metal or $R_4N$ where $R_4$ is straight or branched alkyl of 1 to 6 carbon atoms when $R_5$ is H, in an alcohol solvent, or when M is an alkali metal and $R_5$ is alkyl of 1 to 6 carbon atoms in an aqueous alcohol solvent to preferentially form a salt 7 wherein X, Y and M are defined as above

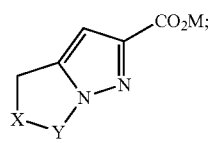

7 b. isolating the salt 7;

c. reacting the salt 7 with acid to form bicyclic-heteroaryl-2-carboxylic acid 8 of the formula wherein X and Y are defined as above

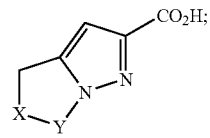

8 d. reacting the bicyclic-heteroaryl-2-carboxylic acid 8 or pharmaceutically acceptable salts thereof with an acid halide reagent or coupling reagent to form an activated intermediate of formula 9 wherein X and Y are defined as above, where Q is a leaving group formed from the coupling reagent or acid halide reagent

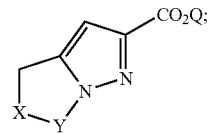

9 e. reacting an activated intermediate of formula 9 or the bicyclic-heteroaryl-2-carboxylic acid 8 with a substituted hydroxylamine of the formula $R_3NHOR_2$ 10 where $R_2$ and $R_3$ are independently alkyl of 1 to 6 carbon atoms in the presence of an organic base or inorganic base to provide an amide of formula 11 wherein X, Y, $R_2$ and $R_3$ are defined as above

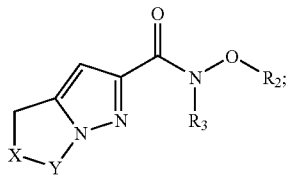

f. reducing the amide of formula 11 with a reducing agent to provide a bicyclic heteroaryl carboxaldehyde of Formula I wherein X and Y are defined as above

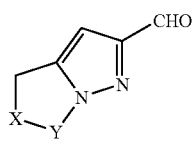

and isolating the bicyclic heteroaryl carboxaldehyde of Formula I.

A further embodiment of this invention provides a process for the preparation of bicyclic-heteroaryl-2-carboxylic acid salt of formula 7

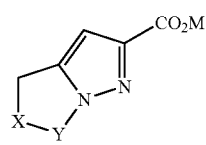

wherein:
Y is $(CH_2)_n$;
n is 1 or 2;
X is NR, O, S, or $CH_2$;
R is alkyl of 1 to 6 carbon atoms, or arylalkyl($C_1$ to $C_6$);
M is an alkali metal;
provided n is 2 when X is NR or O;

which process comprises the steps of:
a. reacting a mixture of bicyclic-heteroaryl-3-carboxylate ester 5 and bicyclic-heteroaryl-2-carboxylate ester 6 wherein $R_1$ is alkyl of 1 to 6 carbon atoms and X and Y are defined as above

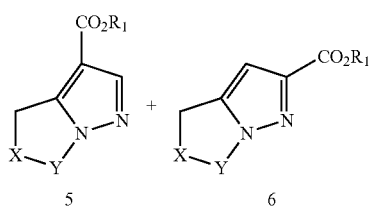

with a hydrolyzing reagent $MOR_5$ where M is an alkali metal or $R_4N$ where $R_4$ is straight or branched alkyl of 1 to 6 carbon atoms when $R_5$ is H, in an alcohol solvent, or when M is an alkali metal and $R_5$ is alkyl of 1 to 6 carbon atoms in an aqueous alcohol solvent to preferentially form a salt 7 of the formula wherein X, Y and M are defined as above

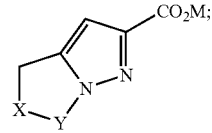

c. isolating the salt 7;
d. optionally reacting the salt 7 with acid to form the bicyclic-heteroaryl-2-carboxylic acid 8 of the formula wherein X and Y are defined as above

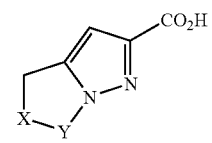

and isolating the bicyclic-heteroaryl-2-carboxylic acid 8.

An additional embodiment of this invention provides an amide of formula 11

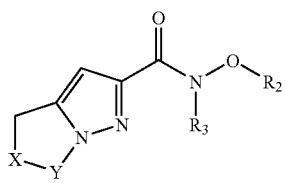

wherein:
Y is $(CH_2)_n$;
n is 1 or 2;
X is NR, O, S, or $CH_2$;
R is alkyl of 1 to 6 carbon atoms, or arylalkyl($C_1$ to $C_6$);
provided n is 2 when X is NR or O;
$R_2$ and $R_3$ are independently alkyl of 1 to 6 carbon atoms.

A preferred embodiment of amide 11 are compounds where X is —$CH_2$—.

In particular compounds of formula 11 include: N-methoxy-N-methyl-5,6-dihydro-4H-pyrrolo[1,2-b]-pyrazole-2-carboxamide.

A further embodiment of this invention additionally provides a compound of formula 7

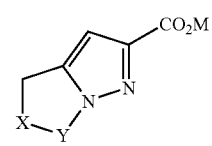

wherein:
Y is $(CH_2)_n$;
n is 1 or 2;
X is NR, O, S, or $CH_2$;

R is alkyl of 1 to 6 carbon atoms, or arylalkyl($C_1$ to $C_6$); provided n is 2 when X is NR or O;

M is an alkali metal.

A preferred embodiment of formula 7 are compounds where M is potassium and X is —$CH_2$—.

In particular compounds of formula 7 include:
potassium salt of 5,6-dihydro-4H-pyrrolo-[1,2-b]pyrazole-2-carboxylic acid.

A further embodiment of this invention includes:

A process for the preparation of bicyclic heteroaryl penem-2-carboxylic acid 16 protected acid, pharmaceutically acceptable salt or preferably an alkali metal salt of the formula

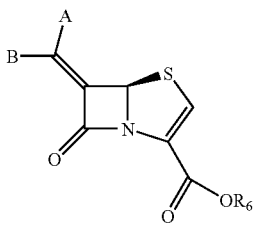

16 wherein:
one of A and B denotes hydrogen and the other a moiety

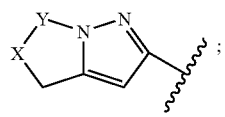

Y is $(CH_2)_n$;
n is 1 or 2;
X is NR, O, S, or $CH_2$;
R is alkyl of 1 to 6 carbon atoms, or arylalkyl($C_1$ to $C_6$); provided n is 2 when X is NR or O;
$R_3$ is alkyl of 1 to 6 carbon atoms;
$R_6$ is H, an in vivo hydrolyzable ester selected from the group $C_1$-$C_6$ alkyl, $C_5$-$C_6$ cycloalkyl, —$CHR_3OCOC_1$-$C_6$, benzyl or p-nitrobenzyl protecting groups or a pharmaceutically acceptable salt, preferably an alkali metal salt;

which process comprises the steps of:
a. nitrosating an amino acid 1 of the formula

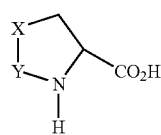

1 wherein X and Y are defined as above with a nitrosating reagent to form a nitroso compound of formula 2 wherein X and Y are defined as above

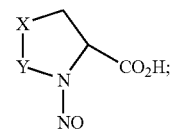

2 b. reacting the nitroso compound 2 with a dehydrating agent and neutralizing with inorganic base to form the ylide of formula 3 wherein X and Y are defined as above

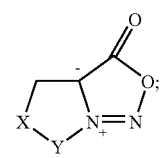

3 c. reacting the ylide of formula 3 with a propiolate ester of formula 4

$$HC\equiv CCO_2R_1 \qquad 4$$

where $R_1$ is alkyl of 1 to 6 carbon atoms, in aprotic solvents to form a mixture of bicyclic-heteroaryl-3-carboxylic acid ester 5 and bicyclic-heteroaryl-2-carboxylic acid ester 6 wherein $R_1$, X and Y are defined as above

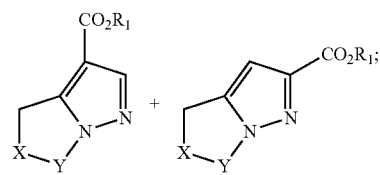

5    6 d. reacting the mixture of bicyclic-heteroaryl-3-carboxylic ester 5 and bicyclic-heteroaryl-2-carboxylic ester 6 with a hydrolyzing reagent $MOR_5$ where M is an alkali metal or $R_4N$ where $R_4$ is straight or branched alkyl of 1 to 6 carbon atoms when $R_5$ is H, in an alcohol solvent, or when M is an alkali metal and $R_5$ is alkyl of 1 to 6 carbon atoms in an aqueous alcohol solvent to preferentially form a salt 7 of the formula wherein X, Y and M are defined as above

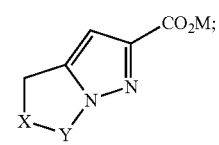

7 e. isolating the salt 7;
f. reacting the salt 7 with mineral acid to form bicyclic-heteroaryl 2-carboxylic acid 8 of formula

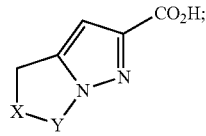

g. reacting the bicyclic-heteroaryl-2-carboxylic acid 8 or salts thereof with an acid halide reagent or coupling reagent to form an activated intermediate of formula 9 where Q is a leaving group formed from the coupling reagent or acid halide reagent wherein X and Y are defined as above

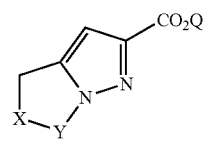

reacting an activated intermediate of formula 9 or the bicyclic-heteroaryl-2-carboxylic acid 8 with a substituted hydroxylamine of the formula $R_3NHOR_2$ 10 where $R_2$ and $R_3$ are independently alkyl of 1 to 6 carbon atoms in the presence of an organic base to provide an amide of formula 11 wherein X, Y, $R_2$, and $R_3$ are defined as above

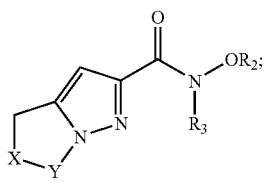

h. reducing the amide of formula 11 with a reducing agent to provide a bicyclic heteroaryl carboxaldehyde of Formula I wherein X, Y, $R_2$ and $R_3$ are defined as above

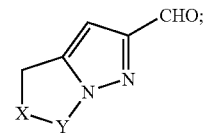

i. condensing the bicyclic heteroaryl carboxaldehyde of Formula I with bromo-penem 13 of the formula

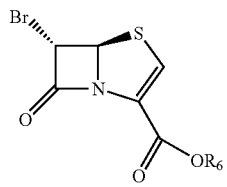

$R_6$ having a protected acid where $R_6$ is an in vivo hydrolyzable ester selected from the group $C_1$-$C_6$ alkyl, $C_5$-$C_6$ cycloalkyl, and —$CHR_3OCOC_1$-$C_6$ or additionally benzyl or p-nitrobenzyl protecting groups;

in the presence of a Lewis acid, and a mild base to form an aldol 14 of the formula wherein X, Y and $R_6$ are defined as above

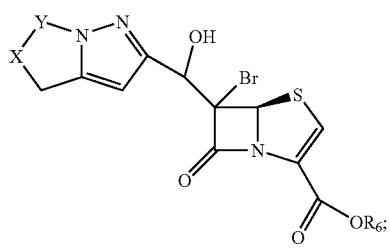

j. reacting aldol 14 with an acid chloride or anhydride, $(R_4)Cl$ or $(R_4)_2O$, or with tetrahalomethane, $C(X_1)_4$, and triphenyl phosphine, to form intermediate compound 15 wherein $R_4$ is alkyl$SO_2$, aryl$SO_2$, alkylCO, or arylCO; $X_1$ is Br, I, or Cl; X, Y and $R_6$ are as defined above; and $R_5$ is $X_1$ or $OR_4$; and

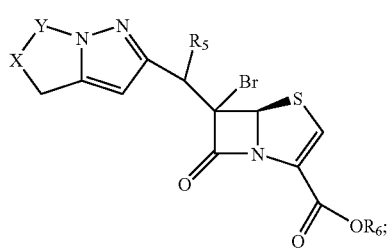

k. converting the intermediate compound 15 by a reductive elimination process to the bicyclic-heteroaryl-penem-2-carboxylic acid 16 where $R_6$ is H and A and B are defined as above and if desired converting to an ester wherein $R_6$ is $C_1$-$C_6$ alkyl, $C_5$-$C_6$ cycloalkyl, or —$CHR_3OCOC_1$-$C_6$, a pharmaceutically acceptable salt preferably an alkali metal salt of the formula

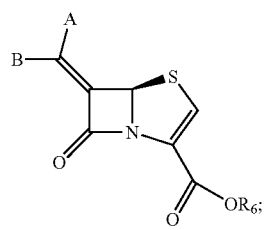

and isolating the bicyclic-heteroaryl-penem-2-carboxylic acid 16 preferably as an alkali metal salt.

The invention further provides a process for the preparation of a compound having Formula I or 16 which process comprises reducing a compound having formula 11 to provide a bicyclic heteroaryl carboxaldehyde having Formula I and, where a compound having formula 16 is desired, converting the bicyclic heteroaryl carboxaldehyde having Formula I into the compound having formula 16. The compound having formula 16 may be prepared from the bicyclic heteroaryl carboxaldehyde having formula I in the manner described in WO 03/093279.

DETAILED DESCRIPTION OF THE INVENTION

As described in Scheme I, amino acid 1 (L, D or racemic) where X, Y, are hereinbefore described are nitrosated in the presence of a nitrosating reagent which includes sodium nitrite and hydrochloric acid to afford 1-nitroso-amino acid 2 which is further reacted with a dehydrating agent, which includes but not limited to trifluoroacetic anhydride, by using the described method (Ranganathan, D.; Shakti, B. "A Novel Proline Derived Meso-Ionic Synthon." *Tetrahedron Letts*. 1983: 24 (10); 1067-1070) with work-up modifications which include neutralization of the reaction mixture with an aqueous solution of an inorganic base such a potassium bicarbonate, or potassium carbonate (and the like) or an anhydrous inorganic base such as powdered potassium carbonate and extraction of the desired product with a solvent such as dichloromethane which eliminates the need for chromatography, to prepare ylide 3. Reaction of ylide 3 with propiolate esters 4 where $R_1$ is alkyl of 1 to 6 carbon atoms, such as ethyl propiolate using the method (Ranganathan, D.; Shakti, B. "A Novel Proline Derived Meso-Ionic Synthon." *Tetrahedron Letts*. 1983: 24 (10); 1067-1070), preferably $R_1$ is methyl or ethyl, in aprotic solvents, which include substituted aromatic hydrocarbons, (e.g. chlorobenzene, mesitylene and the like), substituted amides (e.g. N,N-dimethylformamide, N,N-dimethylacetamide and the like), sulfoxides (e.g. dimethyl sulfoxide and the like) and ethers (e.g. ethers of ethylene glycol such as 1,2-diethyl, 1,2-dimethyl and the like) affords a mixture of bicyclic-heteroaryl-3-carboxylate ester 5 and bicyclic-heteroaryl-2-carboxylate ester 6 wherein $R_1$, X and Y are as defined above. Preferred reaction temperatures are in the range of about 100-165° C. Preferred solvents are ethers of ethylene glycol (diethyl, dimethyl and the like) substituted amides (N,N-dimethylformamide) and substituted aromatic hydrocarbons such as chlorobenzene in which a mixture of esters, bicyclic-heteroaryl-3-carboxylate ester 5 and bicyclic-heteroaryl-2-carboxylate 6 are formed in a ratio, in the range of about 1.5:1 to about 3:1 favoring the desired bicyclic-heteroaryl-2-carboxylate 6. Especially preferred solvents include diethyl ethylene glycol (1,2-diethoxyethane, DEE), or chlorobenzene wherein the reaction is complete in about 8-12 hours at a reaction temperature of about 120-125° C. and provides a mixture of bicyclic-heteroaryl-2-carboxylate ester 6 and bicyclic-heteroaryl-3-carboxylate ester 5, in a ratio in the range of about 1.5:1 to about 2.5:1 in a ratio favorable to the desired bicyclic-heteroaryl-2-carboxylate ester 6, with little contamination from polymeric materials.

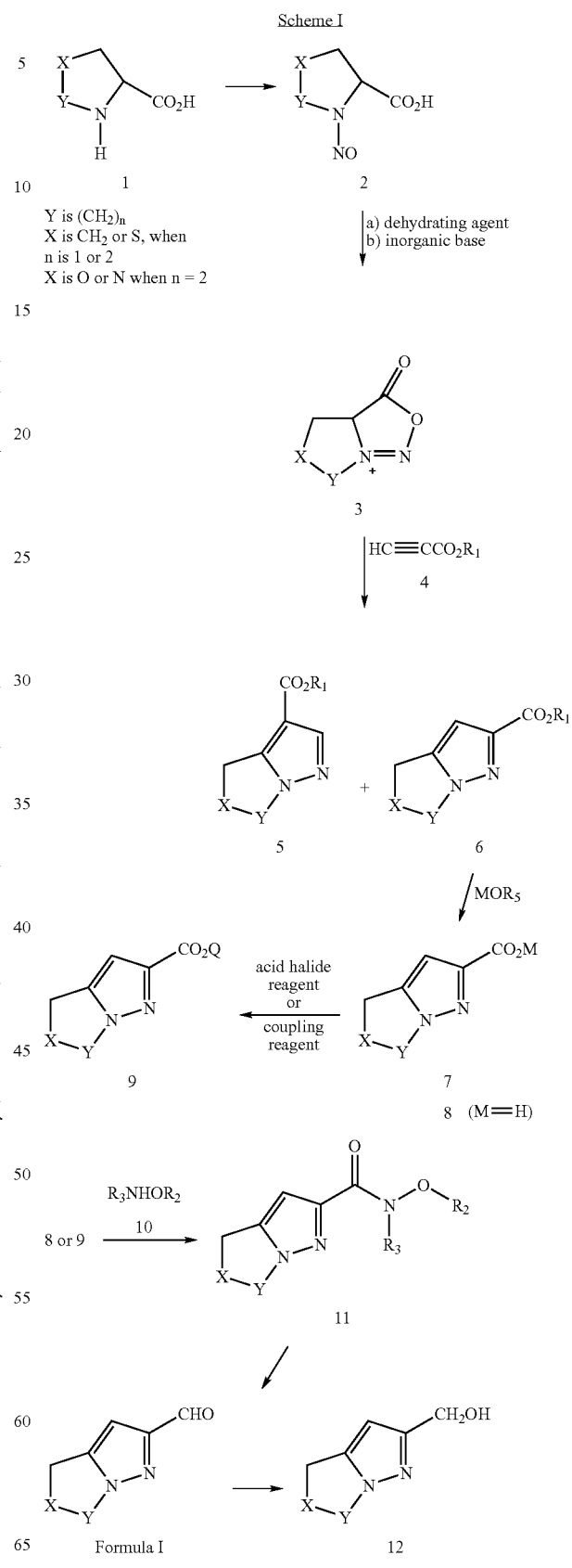

Scheme I

Y is $(CH_2)_n$
X is $CH_2$ or S, when n is 1 or 2
X is O or N when n = 2 a) dehydrating agent
b) inorganic base 8 (M=H)

Formula I

In a mixture of bicyclic-heteroaryl-2-carboxylate ester 6 and bicyclic-heteroaryl-3-carboxylate ester 5 the bicyclic-heteroaryl-2-carboxylate ester 6 is selectively hydrolyzed over the bicyclic-heteroaryl-3-carboxylate ester 5 in a suitable solvent, preferably an alcohol solvent, most preferably ethyl alcohol by reacting with a hydrolyzing reagent $MOR_5$ where $R_5$ is H and M is an alkali metal salt selected from the group consisting of lithium, sodium and potassium or optionally M is $R_4N$ to afford bicyclic-heteroaryl-2-carboxylic acid 7, in particular, where M is an alkali metal salt, preferably sodium or potassium.

The stoichiometry (moles) of hydrolyzing reagent $MOR_5$ where $R_5$ is H and M is an alkali metal salt is at least equivalent to the stoichiometric (moles) of the bicyclic-heteroaryl-2-carboxylate 6 and may optionally be up to 2 times the total quantity (moles) of the bicyclic-heteroaryl 2-carboxylate ester 6 and bicyclic-heteroaryl-3-carboxylate ester 5. Suitable solvents used are typically alcohols, straight chain or branched of 1 to 6 carbon atoms. The reaction time is dependant on temperature, solvent, the hydrolyzing reagent $MOR_5$, in particular an alkali metal hydroxide where M is an alkali metal and $R_5$ is H (and its quantity) and the type of ester (methyl, ethyl, propyl and the like) present in the bicyclic-heteroaryl-2-carboxylate ester 6 and bicyclic-heteroaryl-3-carboxylate ester 5. The reaction temperature may be in the range of about 0-50° C. and the reaction time may be in the range of about 0.5-48 hours. The alkali metal salt bicyclic-heteroaryl-2-carboxylic acid 7 of bicyclic-heteroaryl-2-carboxylic acid 8 can be isolated by direct crystallization of the salt from the reaction medium or crystallization maybe optionally induced by the addition of a non polar, solvent such as ether, tert-butylmethyl ether, hexane, heptane and the like. Optionally, bicyclic-heteroaryl-2-carboxylate ester 6 may be isolated by chromatographic methods before reacting with a hydrolyzing reagent $MOR_5$, in particular an alkali metal hydroxide where M is an alkali metal and $R_5$ is H or where M is $R_4N$ as described hereinbefore. Preferred alkali metal hydroxides include sodium or potassium hydroxide where M is sodium and potassium. Most particularly preferred, M is potassium.

Preferred reaction solvents are alcohols selected from methanol, ethanol, 1-propanol and 2-propanol. Preferred reaction temperatures are in the range of about 15-40° C. Especially preferred is the alkali metal hydroxide, potassium hydroxide (85% w/w) in reaction solvent 2B (anhydrous) ethanol in the temperature range of about 15-30° C. Said especially preferred method is used for the preparation of the especially preferred, potassium salt of 5,6-dihydro-4H-pyrrolo[1,2-b]pyrazole-2-carboxylate, using a ratio in the range of about 1.5:1 to about 2.5:1 mixture of the ethyl esters, ethyl 5,6-dihydro-4H-pyrrolo[1,2-b]pyrazole-2-carboxylate and ethyl 5,6-dihydro-4H-pyrrolo[1,2-b]pyrazole-3-carboxylate, respectively. The product, potassium 5,6-dihydro-4H-pyrrolo-[1,2-b]pyrazole-2-carboxylate, is obtained in at least 81% yield (after a reaction time of about 4-7 hours at about 15-22° C.). However, if impurities (such as potassium 5,6-dihydro-4H-pyrrolo-[1,2-b]pyrazole-3-carboxylate) are present they may optionally be removed by slurrying in 2B ethanol (anhydrous).

The alkali metal salts of bicyclic-heteroaryl-2-carboxylic acid 7 may be converted to the bicyclic-heteroaryl-2-carboxylic acid 8 by treatment with an aqueous mineral acid (such as hydrochloric or sulfuric acids) and bicyclic-heteroaryl-2-carboxylic acid 8 (M is defined as H) may be isolated by extraction with a suitable organic solvent, such as ethyl acetate.

Optionally in a mixture of bicyclic-heteroaryl-2-carboxylate ester 6 and bicyclic-heteroaryl-3-carboxylate ester 5 the bicyclic-heteroaryl-2-carboxylate ester 6 is selectively hydrolyzed over the bicyclic-heteroaryl-3-carboxylate ester 5 in a suitable solvent, preferably an aqueous alcohol solvent, most preferably ethyl alcohol and in particular 3-A alcohol by reacting with a hydrolyzing reagent $MOR_5$ where $R_5$ is alkyl of 1 to 6 carbon atoms and M is an alkali metal salt selected from the group consisting of lithium, sodium and potassium, more particularly sodium or potassium to afford bicyclic-heteroaryl-2-carboxylic acid 7, in particular, where M is an alkali metal salt, preferably sodium or potassium.

The stoichiometry (moles) of hydrolyzing reagent $MOR_5$ where $R_5$ is alkyl of 1 to 6 carbon atoms and M is an alkali metal salt is at least equivalent to the stoichiometric (moles) of the bicyclic-heteroaryl-2-carboxylate 6 and may optionally be up to 2 times the total quantity (moles) of the bicyclic-heteroaryl 2-carboxylate ester 6 and bicyclic-heteroaryl-3-carboxylate ester 5. Additionally, the aqueous alcohol has at least 2 times the total quantity (moles) of the bicyclic-heteroaryl 2-carboxylate ester 6 and bicyclic-heteroaryl-3-carboxylate ester 5, as water. A preferred alcohol solvent is 3-A alcohol which has about 7% water.

As further described in Scheme I, conversion of bicyclic-heteroaryl-2-carboxylic acid 8 (where M is H) and its alkali metal salts (where M is sodium, potassium, lithium and the like) to an activated intermediate 9 is accomplished in several ways. Preferably, reaction of bicyclic-heteroaryl-2-carboxylic acid 8 with acid halide reagents $SO_2Q_2$ or QCO-COQ where Q is chloro or bromo selected from oxalyl chloride, thionyl chloride ($SOCl_2$), and thionyl bromide and the like in an appropriate aprotic solvent (such as dichloromethane, 1,2-dichloroethane, toluene, dimethoxyethane and the like) preferably in the presence of an N,N-dialkylamide catalyst such as N,N-dimethylformamide at an appropriate temperature (−10-30° C.) affords activated intermediate 9 where Q is chloro or bromo. The activated intermediate 9 thus generated is reacted with a substituted hydroxylamine $R_3NHOR_2$ 10 where $R_2$ and $R_3$ are independently alkyl of 1 to 6 carbon atoms [i.e. $R_3NHOR_2$, wherein $R_3$, $R_2$=Me, i.e. O,N-dimethylhydroxylamine and the like] in a suitable solvent such as dichloromethane, toluene, dimethoxyethane and the like, in the presence of an organic base such as triethylamine, N,N-diisopropylethylamine, pyridine and the like, in a temperature range of about −10-50° C., to provide amide 11 wherein X, Y, $R_2$ and $R_3$ are defined as above. A preferred method involves generating the activated intermediate 9 where Q is Cl with oxalyl chloride in dichloromethane at about 0-25° C. in the presence of a catalytic amount of N,N-dimethylformamide and then reacting the activated intermediate 9 where Q is Cl with a substituted hydroxylamine hydrochloride 10 in the presence of an organic base such as pyridine or N,N-diisopropylethylamine in the temperature range of about 0-25° C. to afford amide 11 wherein X, Y, $R_2$ and $R_3$ are defined as above.

Alternatively, the activated intermediate 9 where Q is Cl or Br may be reacted with substituted hydroxylamine hydrochloride 10 in a two phase system such as dichloromethane, toluene, ethyl acetate and the like and water in the presence of an inorganic base such as sodium hydroxide, sodium carbonate, sodium bicarbonate or potassium hydroxide, potassium carbonate, potassium bicarbonate and the like. An especially preferred method for forming the amide 11 wherein X, Y, $R_2$ and $R_3$ are defined as above, is to use Schotten-Baumen conditions in which a solution of the activated intermediate 9 of bicyclic-heteroaryl 2-carboxylic acid where Q is Cl in dichloromethane (generated from thionyl chloride/N,N-dimethylformamide) is reacted with an aqueous solution of substituted hydroxylamine 10 in the presence of an inorganic base, potassium carbonate, in the temperature range of about 10-20° C. In particular, N-methoxy-N-methyl-5,6-dihydro-4H-pyrrolo[1,2-b]pyrazole-2-carboxamide is prepared by Schotten-Baumen conditions without requiring further purification after isolation.

Coupling of a bicyclic-heteroaryl-2-carboxylic acid 8, which includes 5,6-dihydro-4H-pyrrolo[1,2-b]pyrazole-2-carboxylic acid, with a substituted hydroxylamine, 10 (scheme I), to synthesize an amide 11 wherein X, Y, $R_2$ and $R_3$ are defined as above can be accomplished using several procedures.

In a typical coupling procedure, the bicyclic-heteroaryl-2-carboxylic acid 8 and substituted hydroxylamine 10 are combined with a suitable coupling reagent. A suitable coupling reagent converts the carboxylic acid group into a activated intermediate 9 where Q is a leaving group formed from the coupling reagent, such that an amide linkage is formed between the carboxylic acid and the substituted hydroxylamine.

Examples of suitable coupling reagents include 1-(3-dimethylaminopropyl)-3-ethylcarbodiimide hydrochloride-hydroxybenzotriazole (DEC/HBT), carbonyldiimidazole, carbonyldimidazole/hydroxybenzotriazole dicyclohexylcarbodiimide/HBT, dicyclohexylcarbodiimide/N-hydroxysuccinimide, 2-ethoxy-1-ethoxycarbonyl-1,2-dihydroquinoline (EEDQ), 2-chloro-1-methylpyridinium iodide, diphenylphosphinyl chloride (DPPCI), propanephosphonic anhydride (propanephosphonic acid anhydride, PAA), diethylphosphoryl cyanide, phenyldichlorophosphate plus imidazole, benzotriazol-1-yloxytris(dimethylamino)phosphonium hexafluorophosphate (BOP-reagent), N,N'bis[2-oxo-3-oxazolidinyl]phosphorodiamidic chloride (BOB Cl), 2-(1H-benzotriazole-1-yl)-1,1,3,3-tetramethyluronium tetrafluoroborate, 2-(1H-benzotriazole-1-yl)-1,1,3,3-tetramethyluronium hexafluorophosphate, bromo-tris-pyrrolidino-phosphonium hexafluorophosphate and benzotriazole-1-yl-oxy-tris-pyrrolidino-phosphonium hexafluorophosphate. The coupling reaction may optionally be in several steps or in a telescoped process.

A typical coupling reaction is generally performed in an inert solvent, preferably an aprotic solvent at a temperature of about –20° C. to about 50° C. for about 1 to about 48 hours, optionally in the presence of a tertiary amine such as, N,N-diisopropylethylamine, N-methylmorpholine, N-methylpyrrolidine, triethylamine, 4-dimethylaminopyridine, 2,6-di-tert.-butyl-4-methylpyridine, pyridine and the like. Suitable solvents include acetonitrile, dichloromethane, ethyl acetate, dimethylformamide, tetrahydrofuran, dioxane or chloroform or mixtures thereof.

In an example of a multistep coupling process, the bicyclic-heteroaryl-2-carboxylic acid 8 is reacted with a coupling reagent to form an activated intermediate 9, where Q is a leaving group, which may optionally be isolated. In a second step, the activated intermediate 9 is then reacted with the substituted hydroxylamine 10 to form the amide 11. Further examples of coupling reagents that convert an acid to an activated intermediate include thionyl chloride, thionyl bromide, oxalyl chloride, cyanuric fluoride, which forms acid fluorides (Q is F), or an alkyl chloroformate such as isobutyl or isopropenyl chloroformate (in the presence of a tertiary amine base), forming a mixed anhydride of the carboxylic acid. An additional example of a coupling reagent for preparing mixed anhydrides is 2,4,6-trichlorobenzoyl chloride [Inanaga et al. Bull. Chem. Soc. Jpn. 52, 1989 (1979)]. The coupling reaction is generally performed in an inert solvent, preferably an aprotic solvent at a temperature of about –20° C. to 30° C. for about 1 to about 24 hours, optionally in the presence of a tertiary amine such as, N,N-diisopropylethylamine, N-methylmorpholine, N-methylpyrrolidine, triethylamine, 4-dimethylaminopyridine, 2,6-di-tert.-butyl-4-methylpyridine, pyridine and the like. Suitable solvents include acetonitrile, dichloromethane, ethyl acetate, dimethylformamide, tetrahydrofuran, dioxane or chloroform or mixtures thereof. The second step for coupling of the activated intermediate 9 has hereinbefore been described where the activated intermediate is prepared from a salt of the carboxylic acid. In the second step when the activated is a mixed anhydride the amine in a suitable solvent, hereinbefore defined, is added to the solution of the mixed anhydride, in the presence of a suitable base, hereinbefore defined, at the temperature used for activation and the temperature is slowly adjusted to about 30° C. The amine is added to the solution at the temperature used for activation and the temperature is slowly adjusted to about 30° C. The reaction time is about 1-48 h.

Other examples of coupling reagents which convert a carboxylic acid into an activated intermediate, optionally isolated, such as an activated ester, include pentafluorophenyl trifluoroacetate which provides an activated phenolic ester. In particular, simple esters such as methyl, ethyl and propyl, made by reaction of 5,6-dihydro-4H-pyrrolo[1,2-b] pyrazole-2-carboxylic acid with the corresponding alcohols using conventional methods, may also serve as activated intermediates. Coupling reagents that provide an activated intermediate, such as, an acyl azide further include diphenylphoshoryl azide. Coupling reagents that provide an activated intermediate, such as, an acyl cyanide include diethylphosphoryl cyanide.

The coupling reaction is in general carried out between about –30° C. and 60° C. conveniently at or below 0° C. In the second step, the substituted hydroxylamine is added to the solution of activated intermediate 9 at the temperature used for activation and the temperature is slowly adjusted to about 30° C. The reaction time is about 1-96 h. Additional coupling reagents are hereinbefore defined.

Reducing the amide 11 wherein X, Y, $R_2$ and $R_3$ are defined as above to produce the bicyclic heteroaryl carboxaldehyde, of Formula I may be effected with a reducing agent which includes an excess of hydride reagents, selected from lithium aluminum hydride and disobutyl aluminum hydride [DIBAL(H)] in solvents, such as tetrahydrofuran, ether and toluene at temperatures between about –10 and 25° C. The use of lithium aluminum hydride in tetrahydrofuran at temperatures in the range of about 0-25° C. is preferred. An especially preferred method is described wherein the reducing reagent is lithium aluminum hydride [0.5 mol per mol. of amide] and the reaction solvent is tetrahydrofuran. The reaction temperature is kept at about 0-5° C. for about 18 hours. To reduce the quantity of a by-product, alcohol 12, generated on quenching the reaction mixture with water, the reaction mixture is preferentially, quenched by adding the reaction mixture to a solution of tetrahydrofuran and water. Acid extraction with dichloromethane is preferred. Especially preferred is purification of the bicyclic heteroaryl carboxaldehyde, of Formula I via a water soluble, sodium bisulfite complex which in particular effectively removes residual alcohol 12.

As further described in Scheme II bicyclic-heteroaryl-penem-2-carboxylic acid 16, protected acid or pharmaceutically acceptable salt thereof, preferably an alkali metal salt where, one of A and B denotes a hydrogen and the other a moiety

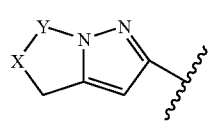

wherein X and Y are defined as above, can be prepared by condensing bicyclic heteroaryl carboxaldehydes 11 prepared as described in Scheme I with 6-bromo-penem 13 having a protected acid where $R_6$ is an in vivo hydrolyzable ester selected from the group $C_1$-$C_6$ alkyl, $C_5$-$C_6$ cycloalkyl, and $CHR_3OCOC_1$-$C_6$ wherein $R_3$ is defined as above or additionally benzyl or p-nitrobenzyl protecting groups in the presence of a Lewis acid, preferably anhydrous magnesium halide more preferably anhydrous $MgBr_2$ or $MgBr_2$: etherate and a mild base such as triethylamine, dimethylaminopyridine (DMAP), or diisopropyl ethyl amine, at low temperature preferably at about −20° C. to −40° C. to afford aldol 14 which can be functionalized with acid chlorides or anhydrides preferably to an acetate, triflate or a tosylate or optionally can be converted to a halogen derivative by reaction with tetrahalomethane and triphenyl phosphine at room temperature in a suitable organic solvent preferably $CH_2Cl_2$ to give intermediate 15. Reacting aldol 14 with an acid chloride or anhydride, $(R_4)Cl$ or $(R_4)O$, or with tetrahalomethane, $C(X_1)_4$, and triphenyl phosphine, forms intermediate compound 15 wherein $R_4$ is alkylSO$_2$, alkylCO, or arylCO; $X_1$ is Br, I, or Cl; A and R are as defined above; and $R_6$ is $X_1$ or $OR_4$. The intermediate 15 can be converted to the desired bicyclic-heteroaryl-penem-2-carboxylic acid 16 protected acid or pharmaceutically acceptable salt thereof, preferably an alkali metal salt by a reductive elimination process using a metal such as activated zinc and phosphate buffer at mild temperatures preferably about 20° C. to 35° C. at a pH of about 6.5 to 8.0 or hydrogenating over a catalyst preferably palladium on charcoal. It should be noted that the reductive elimination step could be conducted such that deprotection of the carboxyl group occurs. If the protecting group on the carboxylate oxygen is para-nitrobenzyl substituent then the reductive elimination and deprotection can be achieved by a single step. However if the protecting group is other than para-nitrobenzyl substituent, a two step procedure can be followed depending up on the nature of the protecting group. The product can be isolated as a free acid or as a pharmaceutically acceptable salt, preferably as an alkali metal salt. The above mentioned two step procedure can be carried out in one step by carrying out the entire process without isolating the intermediate 15. Additionally, the free acid or alkali metal salt may be converted to an ester where $R_6$ is $C_1$-$C_6$ alkyl, $C_5$-$C_6$ cycloalkyl, and —$CHR_3OCOC_1$-$C_6$.

Scheme II

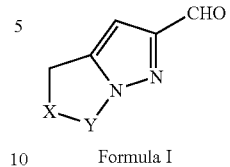

Formula I

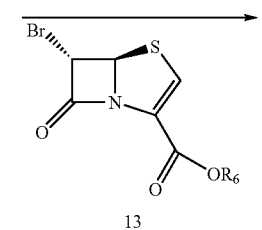

13

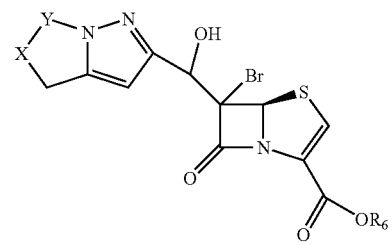

14

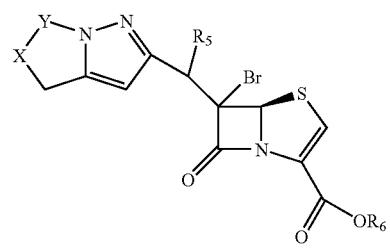

15

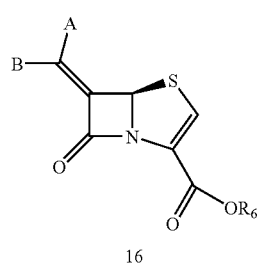

16

The invention is further described in connection with the following non-limiting examples.

EXAMPLE 1

(2S)-1-Nitrosoproline

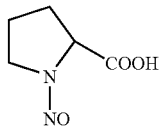

To a solution of L-proline (2.50 kg, 21.6 moles) and sodium nitrite (2.10 kg, 30.4 moles) in water (5.0 L) maintained at 0-10° C. is added concentrated hydrochloric acid (2.53 L) and the resulting slurry is stirred for 16 hours at ambient temperature. The reaction mixture is extracted with t-butyl methyl ether (1×6 L+2×3 L) and the organic solution is concentrated using a rotary evaporator with a bath temperature below 35° C. Residual water is removed by evaporation with 2.0 L of toluene. The resulting (2S)-1-nitrosoproline (3.25 kg, 105%) is isolated as a yellow solid and dried under vacuum at 25° C., m.p. 100-102° C., HPLC purity, 96.3% (area % HPLC conditions described in Example 7) and residual toluene, 4%. The product of the example is used directly, without further purification, in the next step (see example 2).

EXAMPLE 2

3a,4,5,6-Tetrahydro-3-oxo-3H-pyrrolo[1,2-c][1,2,3] oxadiazol-7-ium Ylide

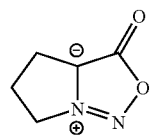

Trifluoroacetic anhydride (3.86 kg, 18.4 moles) is added slowly to a slurry of (2S)-1-nitrosoproline (1.75 kg, 12.2 moles from example 1) in toluene (6 L) below 10° C. The resulting dark-red solution is stirred for 2 hours at ambient temperature and the reaction is quenched by adding the dark-red solution to a stirred mixture of potassium carbonate (2.70 kg, 19.6 moles), dichloromethane (3.5 L) and water (2.0 L) below 25° C. Following complete addition and after separating the upper organic layer, the aqueous layer is extracted with dichloromethane (3×3.0 L). The combined organic extracts are concentrated under vacuum using a rotary evaporator with a bath temperature at 35-45° C. Residual water is removed by evaporation with toluene (2.0 L) to afford the title compound as a dark liquid, which solidified upon standing (0.91 kg, 58% yield over 2 steps). The product of the example, 3a,4,5,6-tetrahydro-3-oxo-3H-pyrrolo[1,2-c][1,2,3]oxadiazol-7-ium ylide, is 89.8% pure by HPLC (area % HPLC conditions described in Example 17) and by HPLC strength, 92.9% and by GC-MS the purity is 99.2%. The product of the example is used directly in the next step (see example 5).

EXAMPLE 3

3a,4,5,6-Tetrahydro-3-oxo-3H-pyrrolo[1,2-c][1,2,3] oxadiazol-7-ium Ylide

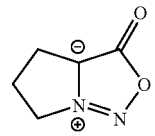

To a solution of (2S)-1-nitroso-proline (9.20 g, 0.0638 mol) in dichloromethane (50 mL) under nitrogen at 0-5° C. is added trifluoroacetic anhydride (12 mL, 0.0850 mol) dropwise over a period of 10 minutes. After 15 minutes all the solid had dissolved and the solution started to turn colored. After a total reaction time of 20 minutes the dark solution is poured into a magnetically stirred mixture of potassium bicarbonate (22 g) and water (50 ml) using dichloromethane (50 mL) as a rinse. The lower organic phase is separated and the dark colored, aqueous phase is extracted with dichloromethane (3×50 mL). The combined organic extracts are dried over anhydrous magnesium sulfate overnight. The drying agent is collected on a filter and washed with dichloromethane (50 mL). The dark red filtrate and washings are evaporated to a dark red, mobile, oil (7.17 g, 89%) which crystallized on seeding with material prepared as in example 2. The product of the example, 3a,4,5,6-tetrahydro-3-oxo-3H-pyrrolo[1,2-c][1,2,3]oxadiazol-7-ium ylide, is 91.8% pure by HPLC (area %, see example 17 for HPLC method).

EXAMPLE 4

3a,4,5,6-Tetrahydro-3-oxo-3H-pyrrolo[1,2-c][1,2,3] oxadiazol-7-ium Ylide

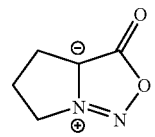

To a stirred solution of (2S)-1-nitrosoproline (57.6 g, 0.4 mole, example 1) in acetonitrile (400 ml) below 10° C. is added slowly, trifluoroacetic anhydride (107 g, 72 ml, 0.51 mole). The resulting, stirred, dark-red solution is allowed to warm to ambient temperature over a period of 2 hours. Potassium carbonate (anhydrous, powdered, 75 g, 0.54 mole) is then added, in portions, to the stirred solution and the resulting mixture is stirred at ambient temperature for 1 hour. The mixture is filtered and the filtrate is evaporated to dryness under diminished pressure to a residue. The residue is then mixed with dichloromethane (2.5 L). The initial ylide, by GC-MS analysis). The mixture is then concentrated under oil pump vacuum using a rotary evaporator with a bath temperature up to 70° C. to a residue. About 1.5 kg of toluene is then added to the residue and the mixture is concentrated once more. A dark oil is obtained [1218 g, 46.9% strength, (HPLC) in 41% (real yield of ethyl 5,6-dihydro-4H-pyrrolo[1,2-b]pyrazole-2-carboxylate, from crude 3a,4,5,6-tetrahydro-3-oxo-3H-pyrrolo[1,2-c][1,2,3]oxadiazol-7-ium ylide].

| Solvent | Temp° C. | Addition Time (hours)* | Hold Time (hours)** | Ylide, 3, starting (g) | Product Crude (g) | 2-Ester Wt % | 2-Ester % Yield (crude to real) | Ratio of 2-Ester to 3-Ester by GC-MS (Area %) |
|---------|----------|-----------------------|--------------------|-----------------------|-------------------|--------------|--------------------------------|----------------------------------------------|
| DEE | 120–125 | 3 | 5 | 971 | 1218 | 46.9 | 41 | 58/42 |
| DEE | 120–125 | 3 | 6.2 | 1400 | 1988 | 48.2 | 47 | 60/37 |
| DEE | 120–125 | 3 | 8 | 827 | 1075 | 45.5 | 42 | 57/40 |

*Addition time is the time taken to add the reagent, ethyl propiolate.
**Hold time is the time the reaction is allowed to run beyond the addition time. The total reaction time is the sum of the addition time and the hold time.

glassy, dark brown mass largely dissolved giving a suspension of inorganic materials. The suspension is filtered and the filter pad is washed with dichloromethane. The filtrates are evaporated under diminished pressure to afford 46 g (91%) of 3a,4,5,6-tetrahydro-3-oxo-3H-pyrrolo[1,2-c][1,2,3]oxadiazol-7-ium ylide as a dark liquid that solidified upon standing; m.p. 33-38° C. and the 3a,4,5,6-tetrahydro-3-oxo-3H-pyrrolo[1,2-c][1,2,3]oxadiazol-7-ium ylide is used directly in the next step (see example 7).

EXAMPLE 5

Ethyl 5,6-dihydro-4H-pyrrolo[1,2-b]pyrazole-2-carboxylate, and Ethyl 5,6-dihydro-4H-pyrrolo[1,2-b]pyrazole-3-carboxylate, by Cycloaddition of 3a,4,5,6-Tetrahydro-3-oxo-3H-pyrrolo[1,2-c][1,2,3]oxadiazol-7-ium Ylide With Ethyl Propiolate in 1,2-Diethoxyethane

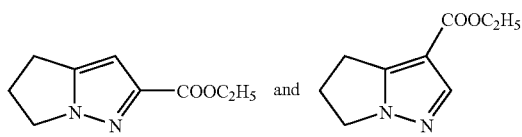

The 3a,4,5,6-Tetrahydro-3-oxo-3H-pyrrolo[1,2-c][1,2,3]oxadiazol-7-ium ylide (971 g, 7.70 mol, made as in example 2) and 1,2-diethoxyethane (DEE, 2913 mL) are charged to a multinecked 12 L round bottom flask, is equipped with a water cooled condenser, and purged with nitrogen. The stirred solution is heated to 120-125° C. under a nitrogen atmosphere and ethyl propiolate (971 g, 9.90 mol) is added dropwise over a period of 3 hours (carbon dioxide evolution). The reaction is held at 120-125° C. for about 5 hours until the conversion is >99% (<1% of residual 3a,4,5,6-tetrahydro-3-oxo-3H-pyrrolo[1,2-c][1,2,3]oxadiazol-7-ium

EXAMPLE 6

Ethyl 5,6-dihydro-4H-pyrrolo[1,2-b]pyrazole-2-carboxylate, and Ethyl 5,6-dihydro-4H-pyrrolo[1,2-b]pyrazole-3-carboxylate by Cycloaddition of 3a,4,5,6-Tetrahydro-3-oxo-3H-pyrrolo[1,2-c][1,2,3]oxadiazol-7-ium Ylide With Ethyl Propiolate in Chlorobenzene

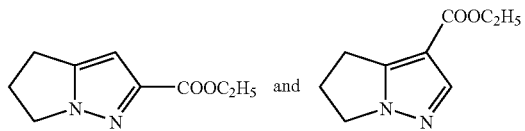

To 3a,4,5,6-Tetrahydro-3-oxo-3H-pyrrolo[1,2-c][1,2,3]oxadiazol-7-ium Ylide (29.3 g, 0.232 mol prepared as in example 2) and chlorobenzene (97.2 g) under a nitrogen atmosphere at 120-125° C. is added dropwise ethyl propiolate (29.3 g, 0.299 mol) over a period of about 2 hours (carbon dioxide evolution). The reaction is held for about 3 hours until the conversion is >99% (<1% residual according to GC-MS analysis). The GC-MS ratio of the desired isomer, ethyl 5,6-dihydro-4H-pyrrolo[1,2-b]pyrazole-2-carboxylate, to the undesired isomer, ethyl 5,6-dihydro-4H-pyrrolo[1,2-b]pyrazole-3-carboxylate, is 59/41 The mixture is then washed with water (50 mL). The organic phase is concentrated under oil pump vacuum up to a bath temperature of about 70° C. to afford a residue as a dark oil [39.1 g, 45.3% strength (HPLC) in ethyl 5,6-dihydro-4H-pyrrolo[1,2-b]pyrazole-2-carboxylate, 42% (real yield of 5,6-dihydro-4H-pyrrolo[1,2-b]pyrazole-2-carboxylate from crude 3a,4,5,6-tetrahydro-3-oxo-3H-pyrrolo[1,2-c][1,2,3]oxadiazol-7-ium ylide)]. The oil is characterized by HPLC, NMR.

EXAMPLE 7

Synthesis and Separation of Ethyl 5,6-Dihydro-4H-pyrrolo[1,2-b]pyrazole-2-carboxylate and Ethyl 5,6-Dihydro-4H-pyrrolo[1,2-b]pyrazole-3-carboxylate

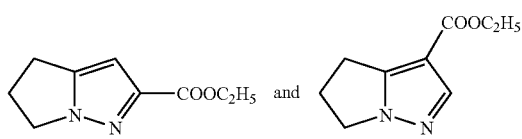

A solution of 3a,4,5,6-tetrahydro-3-oxo-3H-pyrrolo[1,2-c][1,2,3]oxadiazol-7-ium ylide (13.5 g, 0.107 mole, crude, from example 4) and ethyl propiolate (15.8 g, 16.3 ml, 0.16 mole) in dry N,N-dimethylformamide (50 ml) is stirred and heated to 120-122° C. under a nitrogen atmosphere for a period of 12 hours. The reaction is monitored for completion by HPLC [Prodigy ODS3 4.6×150 mm column, with a 10 minutes gradient from 90:10 to 10:90 water/acetonitrile with 0.02% trifluoroacetic acid. Retention times under these conditions were: 2.6-2.7 min for ethyl 5,6-dihydro-4H-pyrrolo[1,2-b]pyrazole-2-carboxylate (the desired, more polar isomer) and 2.8-2.9 min for ethyl 5,6-dihydro-4H-pyrrolo[1,2-b]pyrazole-3-carboxylate (the less polar, undesired isomer). The UV detector was set at 215 nm, because at 254 nm the two isomers absorbed very differently, and the undesired isomer was almost undetectable). The mixture is then evaporated to a dark syrup under oil pump vacuum using a bath temperature up to ~50° C. The ratio of the esters in the dark syrup is determined by NMR, as 2.13 to 1 in favor of the desired ester, ethyl 5,6-dihydro-4H-pyrrolo[1,2-b]pyrazole-2-carboxylate. The dark syrup is diluted with toluene and the solution is applied to a column of silica gel (500 mL) prepacked in hexanes by washing onto the column with hexanes. Elution is with hexanes-ethyl acetate mixture (4:1) followed by hexanes-ethyl acetate (1:1). Fractions are monitored by HPLC (same conditions as above). Fractions that contained both esters are combined and chromatographed once more. Fractions containing only ethyl 5,6-dihydro-4H-pyrrolo[1,2-b]pyrazole-2-carboxylate are combined and concentrated to give 11 g (57%) of the pure ester as white crystals, m. p. 41-43° C. Similarly, 6.5 g (33.7%) of ethyl 5,6-dihydro-4H-pyrrolo[1,2-b]pyrazole-3-carboxylate is obtained as white crystals, m.p. 35-37° C.

EXAMPLE 8

Synthesis of 5,6-Dihydro-4H-pyrrolo[1,2-b]pyrazole-2-carboxylic acid From the Crude Mixture of Esters, Ethyl 5,6-Dihydro-4H-pyrrolo[1,2-b]pyrazole-2-carboxylate and Ethyl 5,6-Dihydro-4H-pyrrolo[1,2-b]pyrazole-3-carboxylate

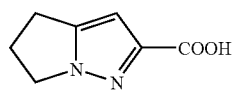

Sodium ethoxide solution, in denaturated ethanol (21 wt %, 12 ml, 38 mmol) is added to 6.9 g (38 mmol) of the crude mixture of esters, ethyl 5,6-dihydro-4H-pyrrolo[1,2-b]pyrazole-2-carboxylate and ethyl 5,6-dihydro-4H-pyrrolo[1,2-b]pyrazole-3-carboxylate in 3A ethanol (containing 3, 7% water, 15 ml) and the mixture is stirred for 10 hours under a nitrogen atmosphere at 15-22° C. Consumption of ethyl 5,6-dihydro-4H-pyrrolo[1,2-b]pyrazole-2-carboxylate, is monitored by HPLC [Prodigy ODS3 4.6×150 mm column, 10 minutes gradient from 90:10 to 10:90 water/acetonitrile with 0.02% trifluoroacetic acid, UV detection at 215 nm. Retention times under these conditions were: 2.6-2.7 min. for ethyl 5,6-dihydro-4H-pyrrolo[1,2-b]pyrazole-2-carboxylate (the desired, more polar isomer), 2.8-2.9 minutes for ethyl 5,6-dihydro-4H-pyrrolo[1,2-b]pyrazole-3-carboxylate (the undesired, less polar isomer) and 0.86 minutes for 5,6-dihydro-4H-pyrrolo[1,2-b]pyrazole-2-carboxylic acid]. The resulting mixture is evaporated under diminished pressure to a residue as a syrup. The syrup is mixed with ether (25 ml), and the resulting precipitate is collected on a filter. The hygroscopic filter cake is washed with diethyl ether (100 ml) and then dissolved in water (10 ml). The pH of the solution is adjusted to a value of 2 with 1N hydrochloric acid and the mixture extracted with ethyl acetate (3×25 ml). The combined organic extract is dried over magnesium sulfate and evaporated to give 5,6-dihydro-4H-pyrrolo[1,2-b]pyrazole-2-carboxylic acid as an off-white solid (1.40 g, 48%), m.p. 140-145° C., which is characterized by NMR, mass spectrum, elemental analysis, and HPLC (Prodigy ODS3 4.6×150 mm column, with a 20 min gradient from 95:5 to 30:70 using water/acetonitrile with 0.02% trifluoroacetic acid and UV detection at 215 nm. The retention time for 5,6-dihydro-4H-pyrrolo[1,2-b]pyrazole-2-carboxylic acid was 7.2 minutes) The product of the example is used directly in the next step (see example 13).

EXAMPLE 9

Synthesis of the Potassium Salt of 5,6-Dihydro-4H-pyrrolo[1,2-b]pyrazole-2-carboxylic acid From the Mixture of Esters, Ethyl 5,6-Dihydro-4H-pyrrolo[1,2-b]pyrazole-2-carboxylate and Ethyl 5,6-Dihydro-4H-pyrrolo-[1,2-b]pyrazole-3-carboxylate

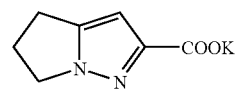

A freshly prepared solution of potassium hydroxide (87.6% w/w pellets, 307.6 g, 4.80 mol) in 2B ethanol (absolute, 1862 mL) is added over a period of 1 hour to a stirred solution of 1063.6 g [46.5% strength (HPLC), 2.744 mol real)] of the ester mixture [(from example 5), ethyl 5,6-dihydro-4H-pyrrolo[1,2-b]pyrazole-2-carboxylate) and ethyl 5,6-dihydro-4H-pyrrolo[1,2-b]pyrazole-3-carboxylate] in 2B ethanol (absolute, 1276 mL) under a nitrogen atmosphere, while maintaining the temperature in the range 15-22° C. The mixture is stirred for 4-7 hours until ethyl 5,6-dihydro-4H-pyrrolo[1,2-b]pyrazole-2-carboxylate, is consumed, as determined by HPLC [Column: Zorbax Eclipse XDB-C8, 4.6×150 mm. Eluant: Acetonitrile/water; wavelength 225 nm. Retention times: potassium 5,6-dihydro-4H-pyrrolo-[1,2-b]pyrazole-2-carboxylate, 1.3 min., ethyl 5,6-dihydro-4H-pyrrolo[1,2-b]pyrazole-2-carboxylate, 6.4 min., ethyl 5,6-dihydro-4H-pyrrolo[1,2-b]pyrazole-3-carboxylate, 7.3 min., N-methoxy-N-methyl-5,6-dihydro-4H-pyrrolo[1,2-b]-pyrazole-2-carboxamide, 2.7 min.] The slurry is filtered and the filter cake is washed with 2B ethanol (1800-2400 ml in portions). The wet cake is dried under vacuum at 60-65° C. to constant weight. Crude potassium 5,6-dihydro-4H-pyrrolo-[1,2-b]pyrazole-2-carboxylate [426.3 g, 81% (based on calcd. quantity of] is obtained as a tan, hygroscopic, solid, which is characterized using NMR, HPLC, KF and ash determinations. The cake may optionally be reslurried in 2B ethanol, if necessary, to remove impurities (such as potassium 5,6-dihydro-4H-pyrrolo-[1,2-b]pyrazole-3-carboxylic acid). The product of the example is used directly in the next step (see example 10).

To a stirred, cold (10-15° C.) slurry of crude potassium 5,6-dihydro-4H-pyrrolo-[1,2-b]pyrazole-2-carboxylate (123.6 g, 0.65 mol, from example 9) in methylene chloride (1234 mL) containing N,N-dimethylformamide (1.8 g) under a nitrogen atmosphere in a 3 L multinecked round bottom flask, fitted with a water cooled condenser, is added thionyl chloride (116.0 g, 0.974 mol) over a period of 45 minutes, while maintaining the temperature below 28° C. The mixture is stirred for about 1 hour and then monitored by HPLC [conditions described in Example 9] until the conversion is >97% to afford the acid chloride. (solution A)

A 5 L multinecked round bottom flask is charged with water (1234 mL), solid potassium carbonate (296.3 g, 2.14 mol) and N,O-dimethylhydroxylamine hydrochloride (95.0 g, 0.97 mol). The mixture is stirred to obtain a clear solution and the solution is cooled to about 10-15° C. (solution B)

| Starting Crude esters 2-Ester/3-Ester (g) | Real 2-Ester (g) | KOH/EtOH Addition Time (hours) | KOH/EtOH Addition Temp ° C. | Reaction Hold Time (hours) | 2-Acid K Salt Product (g) | 2-Acid K Salt % yield real to crude |
|---|---|---|---|---|---|---|
| 587 | 275 | 1 | 20–25 | 4 | 249 | 85 |
| 1064 | 494 | 1 | 17–26 | 4 | 426 | 81 |
| 1967 | 948 | 1.5 | 16–18 | 4 | 816 | 81(a) |
| 2700 | 1150 | 1.2 | 10–20 | 3 | 1039 | 86(a) |

(a)Reslurried with 4 volumes ethyl alcohol to remove residual impurities

EXAMPLE 10

Synthesis of N-Methoxy-N-methyl-5,6-dihydro-4H-pyrrolo[1,2-b]-pyrazole-2-carboxamide From the Potassium Salt of 5,6-Dihydro-4H-pyrrolo[1,2-b]pyrazole-2-carboxylic acid

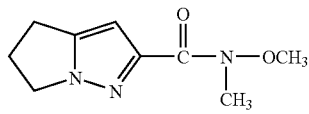

The acid chloride mixture (solution A) is added to (solution B), over a period of 45 minutes while maintaining the temperature at about 10-20° C. The biphasic mixture is stirred for about 1 hour and then checked for completion by HPLC [conditions described in Example 9] The mixture is transferred to a separatory funnel and the lower organic layer is separated. The organic layer is washed with water (1234 mL) and then concentrated under aspirator vacuum initially (and later under oil pump vacuum) using a rotary evaporator, up to a bath temperature of about 90° C. to a residue. On cooling the residue, N-methoxy-N-methyl-5,6-dihydro-4H-pyrrolo[1,2-b]pyrazole-2-carboxamide, (126.8 g, 100%,), is obtained as a tan crystalline solid, mp=56° C., which is characterized by HPLC, NMR, KF and ash determinations. The tan crystalline solid amide, is used directly in the next step (see examples 15 and 16).

| Starting Acid K Salt (g) | SOCl$_2$ Addition Time (hours) | SOCl$_2$ Addition/ Reaction Temp ° C. | Acid Chloride Addition Time (hours) | Acid Chloride Addition Temp ° C. | Product Amide (g) | Product Amide % yield crude to crude |
|---|---|---|---|---|---|---|
| 123.6 | 0.5 | 11–22 | 0.65 | 13–18 | 126 | 100 |
| 413 | 1.0 | 11–34 | 0.65 | 15–20 | 391 | 92 |
| 816 | 1.0 | 15–18 | 1.00 | 10–20 | 871 | 104 (b) |
| 1039 | 1.5 | 16–18 | 1.00 | 15–20 | 1121 | 105 (d) |

(b) ~10% residual amine
(d) ~5% residual amine

EXAMPLE 11

Synthesis of N-Methoxy-N-methyl-5,6-dihydro-4H-pyrrolo[1,2-b]-pyrazole-2-carboxamide From the Potassium Salt of 5,6-Dihydro-4H-pyrrolo[1,2-b]pyrazole-2-carboxylic acid

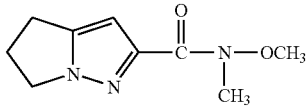

To a cooled (5-6° C.), stirred suspension of crude potassium 5,6-dihydro-4H-pyrrolo[1,2-b]pyrazole-2-carboxylate (21.9 g, 115 mmol) in dichloromethane (180 mL) containing N,N-dimethylformamide (2.5 mL, 32.3 mmol), is added, dropwise, oxalyl chloride (19.0 mL, 218 mmol) over a period of 10 minutes. The reaction is exothermic with gas evolution. After the addition, the ice-bath is removed and the reaction mixture stirred at room temperature. After 5 hours, the solution is added to a cooled, stirred (10-12° C.) suspension of N,O-dimethylhydroxylamine hydrochloride (17.6 g, 180 mmol) in dichloromethane (80 mL) containing N,N-diisopropylethyamine (100 mL, 574 mmol). After 18 hours at room temperature, water (150 mL) is added. The two layers are separated. The organic layer is extracted with water (3×150 mL), and the organic layer dried over anhydrous sodium sulfate, filtered and concentrated under diminished pressure to give a brown solid which is recrystallized from ether (35 mL) to give 15.6 g (69%) of N-methoxy-N-methyl-5,6-dihydro-4H-pyrrolo[1,2-b]-pyrazole-2-carboxamide as a brown solid having HPLC purity, 91.3% (HPLC conditions described in Example 17).

EXAMPLE 12

Synthesis of N-Methoxy-N-methyl-5,6-dihydro-4H-pyrrolo[1,2-b]-pyrazole-2-carboxamide From the Potassium Salt of 5,6-Dihydro-4H-pyrrolo[1,2-b]pyrazole-2-carboxylic acid

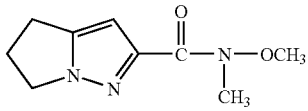

To a cooled (5-6° C.), stirred suspension of crude potassium 5,6-dihydro-4H-pyrrolo[1,2-b]pyrazole-2-carboxylate (0.82 g, 4.3 mmol) in dichloromethane (15 mL), containing N,N-dimethylformamide (0.1 mL, 1.3 mmol), is added, dropwise, oxalyl chloride (0.6 mL, 6.9 mmol). The reaction is exothermic with gas evolution. After the addition, the ice-bath is removed to allow the reaction mixture to stir at room temperature. After 3 hours, the solution is added to a stirred, cooled (10-12° C.) suspension of N,O-dimethylhydroxylamine hydrochloride (0.67 g, 6.9 mmol) in dichloromethane (7 mL) containing pyridine (1.7 mL, 21 mmol). After 40 minutes at room temperature, dichloromethane (35 mL) and water (25 mL) are added. The two layers are separated. The organic layer is extracted with water (2×25 mL), dried over anhydrous sodium sulfate, filtered and concentrated under diminished pressure to give 0.75 g (89% yield) of N-methoxy-N-methyl-5,6-dihydro-4H-pyrrolo[1,2-b]pyrazole-2-carboxamide as a brown solid.

EXAMPLE 13

Synthesis of N-Methoxy-N-methyl-5,6-dihydro-4H-pyrrolo[1,2-b]pyrazole-2-carboxamide From 5,6-Dihydro-4H-pyrrolo[1,2-b]pyrazole-2-carboxylic acid

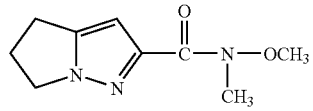

5,6-dihydro-4H-pyrrolo[1,2-b]pyrazole-2-carboxylic acid, 3.8 g, 25 mmol) is slurried in 40 ml of 2M oxalyl chloride in dichloromethane, and to the slurry are added a few drops of dimethylformamide. The resulting mixture is stirred under a nitrogen atmosphere at 15-22° C. for 10-12 hours. The resulting acid chloride as a dark solution is evaporated to a dry residue. The residue is dissolved in toluene (50 ml) and evaporated once more to give the crude acid chloride. To a stirred mixture of the crude acid chloride in dichloromethane (100 ml) and N,O-dimethylhydroxylamine hydrochloride (2.7 g, 27.5 mmol) at 0-5° C. is added pyridine (4.7 g, 3.2 ml, 60 mmol) dropwise under a nitrogen atmosphere while maintaining the temperature about 0-5° C. The resulting stirred mixture is allowed to warm to 15-20° C. over a period of 4 hours and the reaction is monitored for completion by HPLC (Prodigy ODS3 4.6×150 mm column, using a 10 minutes gradient from 90:10 to 10:90 water/acetonitrile with 0.02% trifluoroacetic acid and UV detection at 254 nm. The retention time of the amide was 1.1 min). The mixture is washed with water (50 ml), concentrated, and purified on a short column of silica gel using elution with chloroform to give upon evaporation of volatiles N-Methoxy-N-methyl-5,6-dihydro-4H-pyrrolo[1,2-b]pyrazole-2-carboxamide, 4.1 g, 86%) as a light-brown crystalline solid, m.p. 45-50° C., which is characterized by NMR, mass spectrum, and elemental analysis.

EXAMPLE 14

5,6-Dihydro-4H-pyrrolo[1,2-b]pyrazole-2-carbaldehyde

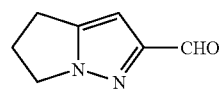

To a solution of N-methoxy-N-methyl-5,6-dihydro-4H-pyrrolo[1,2-b]pyrazole-2-carboxamide, 2.5 g, 12.8 mmol) in tetrahydrofuran (35 mL) cooled to 0-5° C. in an ice/water bath, is added in several portions, lithium aluminum hydride pellets (0.211 g, 5.53 mmol) over a period of 7 hours. The reaction mixture is allowed to warm to room temperature overnight (16 hours). Thin layer chromatography [TLC: EM Science silica gel 60F-254 plate using solvent (20:1) CH$_2$Cl$_2$:CH$_3$OH; Rf 0.66 (5,6-dihydro-4H-pyrrolo[1,2-b]pyrazole-2-carbaldehyde), 0.38 (N-Methoxy-N-methyl-5,6-dihydro-4H-pyrrolo[1,2-b]pyrazole-2-carboxamide) indicated a minor amount of N-methoxy-N-methyl-5,6-dihydro-4H-pyrrolo[1,2-b]pyrazole-2-carboxamide.

The reaction mixture is cooled to 0-5° C. in an ice/water bath and another portion of lithium aluminum hydride (64 mg, 1.68 mmol) is added. After an additional 3 hours at 0-5° C., a saturated solution of sodium sulfate (1.0 mL) is added dropwise to quench the reaction. After 15 minutes, a grayish gel is formed and tetrahydrofuran (50 mL) and magnesium sulfate (2 g) are added. The mixture is stirred for ten minutes and then filtered. The filtrate is concentrated under diminished pressure to give 1.6 g of a clear, colorless oil. To the colorless oil, dichloromethane (25 mL) and 1.5 N hydrochloric acid (5 mL) are added. The organic layer is concentrated under diminished pressure and dried under oil pump vacuum to give 1.31 g (77% yield) of 5,6-dihydro-4H-pyrrolo[1,2-b]pyrazole-2-carbaldehyde, as a white solid, having $^1$H NMR (CDCl$_3$) 2.67-2.75 (m, 2H), 2.95 (t, 2H, J=7.3 Hz), 4.22 (t, 2H, J=7.3 Hz), 6.52 (s, 1H), 9.89 (s, 1H).

EXAMPLE 15

5,6-Dihydro-4H-pyrrolo[1,2-b]pyrazole-2-carbaldehyde

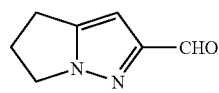

To a stirred, cold (0-5° C.) solution of N-methoxy-N-methyl-5,6-dihydro-4H-pyrrolo-[1,2-b]pyrazole-2-carboxamide (300 g, 1.54 mol, in anhydrous tetrahydrofuran (3.0 L) under a nitrogen atmosphere is added slowly, in portions, lithium aluminum hydride (pellets, 30 g, 0.79 mol) over a period of 0.5 hours. After stirring for 5 hours at 0-5° C. the reaction is quenched by slowly adding saturated sodium sulfate solution (75 mL) to the stirred reaction mixture maintained at 5-15° C. Magnesium sulfate (70 g) is added and the mixture is stirred for 15 minutes. The mixture is then filtered and the filter pad is washed with tetrahydrofuran (1.0 L). The solvent is removed by evaporation at 20-70° C. under diminished pressure to provide a tan-colored oil. The oil is diluted with dichloromethane (1.0 L) and the solution is washed with 1.5 N hydrochloric acid (350 mL). The organic layer is separated and concentrated under aspirator vacuum at 20-70° C. to an oil. Fresh dichloromethane (1.00 L) and water (1.50 L) containing dissolved sodium hydrogensulfite (220 g) are added to the oil. The mixture is stirred for 15 minutes and the phases are separated. The aqueous phase is washed with dichloromethane (2×300 mL). Dichloromethane (1.0 L) and 10 N sodium hydroxide (220 mL) are added (with cooling) to the aqueous phase and the mixture is stirred for 10 minutes The lower organic phase is separated and washed with water (500 mL). The dichloromethane extract is evaporated under diminished pressure at 20-70° C. to give an oil, which crystallizes on cooling, to provide 140.1 g (67%) of 5,6-dihydro-4H-pyrrolo-[1,2-b]pyrazole-2-carbaldehyde, as a white, crystalline solid having, m.p 40-42° C., $^1$H NMR (300 MHz, CDCl$_3$) 2.67-2.75 (m, 2H), 2.95 (t, 2H, J=7.3 Hz), 4.22 (t, 2H, J=7.3 Hz), 6.52 (s, 1H), 9.89 (s, 1H) and HPLC-MS purity, 99.86% at 12.9 minutes:

Column: Xter C18, 100 mm×2.1 mm
Mobile Phase A: H$_2$O:CH$_3$CN 95:5 with 10 m mol of NH$_4$OAc
Mobile Phase B: CH$_3$CN:H$_2$O 95:5 with 10 m mol of NH$_4$OAc
Flow Rate: 0.2 mL/Min
Gradient: T=0 min, Mobile Phase A (80%), Mobile phase B (20%)
T=40 min, Mobile Phase A (0%), Mobile phase B (100%).

EXAMPLE 16

5,6-Dihydro-4H-pyrrolo[1,2-b]pyrazole-2-carbaldehyde

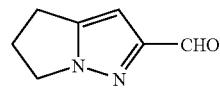

Lithium aluminum hydride (pellets, 2.90 g, 0.0764 mol) is added to a stirred solution of N-methoxy-N-methyl-5,6-dihydro-4H-pyrrolo[1,2-b]pyrazole-2-carboxamide (30.0 g, 0.154 mol) in anhydrous tetrahydrofuran (300 mL) at 0-5° C. and stirred overnight (20 hours) at 0-5° C. under nitrogen. The mixture is then slowly added to a flask containing water (50 ml) and tetrahydrofuran (50 ml) maintained at 5-15° C. Anhydrous sodium sulfate (8.0 g) and anhydrous magnesium sulfate (4.0 g) are added and the mixture is stirred for 0.5 hours. The mixture is filtered, and the filter pad is washed with tetrahydrofuran (100 ml). The filtrate and washings are evaporated under diminished pressure and the residue is stirred for 20 minutes with dichloromethane (150 ml) and 1.5 N hydrochloric acid (40 ml). The phases are separated and water (200 ml) containing dissolved sodium hydrogensulfite (22 g) is added to the organic phase. The mixture is stirred for 20 minutes and the phases are separated. Fresh dichloromethane (150 mL) and 10 N sodium hydroxide (22 mL) are added (with cooling) to the aqueous phase. The mixture is stirred for 20 minutes and the phases are separated. The organic phase is washed with water (100 ml). The dichloromethane extract is evaporated at 20-70° C. to give an oil which crystallizes on cooling to provide 16.1 g (77%) of 5,6-dihydro-4H-pyrrolo-[1,2-b]-pyrazole-2-carbaldehyde as a light yellow, crystalline solid having HPLC-MS purity 99.95% (HPLC conditions as in example 15).

EXAMPLE 17

HPLC Method for Comparison of Retention Times of Compounds Prepared in Examples

| Column: | Synergi- Hydro RP-80 A, 4 µm, 250 × 4.6 mm |  |  |
|---|---|---|---|
| Mobil Phase A: | 950 ml H$_2$O/50 ml ACN/0.5 ml H$_3$PO$_4$ | | |
| Mobil Phase B: | 950 ml ACN/50 ml H$_2$O/0.5 ml H$_3$PO$_4$ | | |
| Gradient: | Time | % A | % B |
|  | 0 | 100 | 0 |
|  | 12 | 100 | 0 |
|  | 45 | 40 | 60 |
|  | 60 | 0 | 100 |
|  | 65 | 0 | 100 |
|  | 65.1 | 100 | 0 |
|  | 75 | 100 | 0 |
| Flow rate: | 1.0 mL/min | | |
| Detection: | 210 nm (226 nm for quantitating the isomer ratio of the esters) | | |

-continued

| | |
|---|---|
| Injection volume: | 6–8 µL |
| Sample solution: | 3.0 mg dissolved in 10 ml ACN:MeOH 1:1 |
| Column temperature: | Ambient |

| Compound | Retention time (min.) |
|---|---|
| (2S)-1-Nitrosoproline | 8.4 |
| 3a,4,5,6-Tetrahydro-3-oxo-3H-pyrrolo-[1,2-c][1,2,3]-oxadiazol-7-ium Ylide | 7.9 |
| Ethyl 5,6-dihydro-4H-pyrrolo[1,2-b]pyrazole-2-carboxylate | 33.1 |
| Ethyl 5,6-Dihydro-4H-pyrrolo-[1,2-b]pyrazole-3-carboxylate | 34.1 |
| 5,6-Dihydro-4H-pyrrolo-[1,2-b]pyrazole-2-carboxylic acid | 23.2 |
| 5,6-Dihydro-4H-pyrrolo-[1,2-b]pyrazole-3-carboxylic acid | 22.2 |
| N-Methoxy-N-methyl-5,6-dihydro-4H-pyrrolo[1,2-b]-pyrazole- 2-carboxamide | 26.6 |
| 5,6-Dihydro-4H-pyrrolo[1,2-b]pyrazole-2-carbaldehyde | 26.2 |

What is claimed is:

1. A process for the preparation of bicyclic heteroaryl carboxaldehydes of Formula I

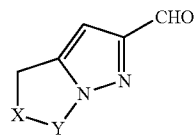

wherein:
  Y is $(CH_2)_n$;
  n is 1 or 2;
  X is $CH_2$;
which process comprises the steps of:
  a. nitrosating an amino acid 1 of the formula

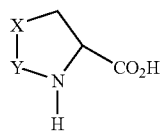

wherein X and Y are defined as above with a nitrosating reagent to form a nitroso compound of formula 2 wherein X and Y are defined as above

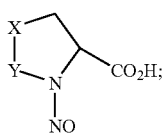

b. reacting the nitroso compound 2 with a dehydrating agent and neutralizing with an inorganic base to form the ylide of formula 3 wherein X and Y are defined as above

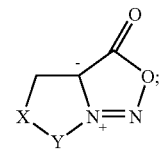

c. reacting the ylide of formula 3 with a propiolate ester of formula 4

$$HC \equiv CCO_2R_1 \qquad 4$$

where $R_1$ is alkyl of 1 to 6 carbon atoms, in aprotic solvents to form a mixture of bicyclic-heteroaryl-3-carboxylate ester of formula 5 and bicyclic-heteroaryl-2-carboxylate ester of formula 6 wherein $R_1$, X and Y are defined as above

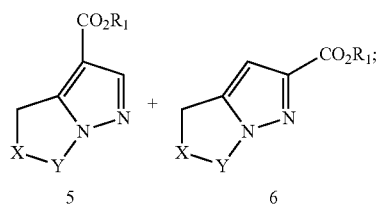

d. reacting the mixture of bicyclic-heteroaryl-3-carboxylate ester 5 and bicyclic-heteroaryl-2-carboxylate ester 6 with a hydrolyzing reagent $MOR_5$ where M is an alkali metal or $R_4N$ where $R_4$ is straight or branched alkyl of 1 to 6 carbon atoms when $R_5$ is H, in an alcohol solvent, or when M is an alkali metal and $R_5$ is alkyl of 1 to 6 carbon atoms in an aqueous alcohol solvent to preferentially form a salt 7 of the formula wherein X, Y and M are defined as above

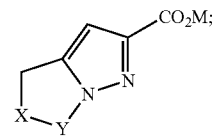

e. isolating the salt 7;
  f. reacting the salt 7 with acid to form bicyclic-heteroaryl-2-carboxylic acid 8 of formula wherein X and Y are defined as above

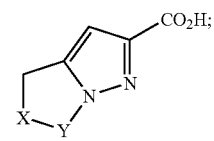

g. reacting the bicyclic-heteroaryl-2-carboxylic acid 8 or salts thereof with an acid halide reagent or coupling reagent to form an activated intermediate of formula 9 where Q is a leaving group formed from the coupling reagent or acid halide reagent wherein X and Y are defined as above

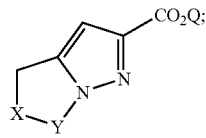

h. reacting an activated intermediate of formula 9 or the bicyclic-heteroaryl carboxylic acid 8 with a substituted hydroxylamine of the formula $R_3NHOR_2$ 10 where $R_2$ and $R_3$ are independently alkyl of 1 to 6 carbon atoms in the presence of an organic base or inorganic base to provide an amide of formula 11 wherein X, Y, $R_2$ and $R_3$ are defined as above

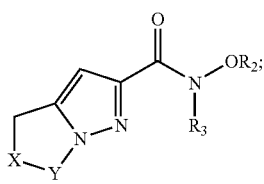

i. reducing the amide of formula 11 with a reducing agent to provide a bicyclic heteroaryl carboxaldehyde of Formula I wherein X and Y are defined as above

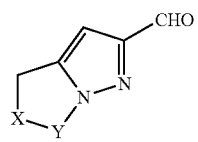

and isolating the heteroaryl carboxaldehyde of Formula I.

2. A process according to claim 1 wherein the nitrosating reagent is sodium nitrite in hydrochloric acid.

3. A process according to claim 1 wherein $R_1$ is methyl or ethyl.

4. The process according to claim 1 wherein the dehydrating agent is trifluoroacetic anhydride.

5. A process according to claim 1 wherein the aprotic solvent is N,N-dimethylformamide, chlorobenzene or 1,2-diethoxyethane at a temperature of about 100-165° C.

6. A process according to claim 5 wherein the aprotic solvent is 1,2-diethoxyethane or chlorobenzene at a temperature of about 120-125° C. forming a mixture of bicyclic-heteroaryl-3-carboxylate ester 5 and bicyclic-heteroaryl-2-carboxylate ester 6 in a ratio, in the range of about 1:1.5 to about 1:2.5.

7. A process according to claim 1 wherein up to 2 moles of hydrolyzing reagent $MOR_5$ in ethanol is used where M is sodium or potassium and $R_5$ is H.

8. A process according to claim 7 wherein M is potassium.

9. A process according to claim 1 wherein the acid is selected from hydrochloric or sulfuric.

10. A process according to claim 1 wherein the acid halide reagent is $SO_2Q_2$ or QCOCOQ where Q is chloro or bromo.

11. A process according to claim 10 wherein the acid halide reagent is selected from thionyl bromide, thionyl choride and oxalyl chloride.

12. A process according to claim 11 wherein the acid halide reagent is oxalyl chloride.

13. A process according to claim 1 wherein the coupling reagent is selected from 1-(3-dimethylaminopropyl)-3-ethylcarbodiimide hydrochloride-hydroxybenzotriazole (DEC/HBT), carbonyldiimidazole, carbonyldimidazole/hydroxybenzotriazole dicyclohexylcarbodiimide/HBT, dicyclohexylcarbodiimide/N-hydroxysuccinimide, 2-ethoxy-1-ethoxycarbonyl-1,2-dihydroquinoline (EEDQ), 2-chloro-1-methylpyridinium iodide, diphenylphosphinyl chloride (DPPCl), propanephosphonic anhydride (propanephosphonic acid anhydride, PAA), diethylphosphoryl cyanide, phenyldichlorophosphate plus imidazole, benzotriazol-1-yloxytris(dimethylamino)phosphonium hexafluorophosphate (BOP-reagent), N,N'bis[2-oxo-3-oxazolidinyl]phosphorodiamidic chloride (BOB Cl), 2-(1H-benzotriazole-1-yl)-1,1,3,3-tetramethyluronium tetrafluoroborate, 2-(1H-benzotriazole-1-yl)-1,1,3,3-tetramethyluronium hexafluorophosphate, bromo-tris-pyrrolidino-phosphonium hexafluorophosphate, benzotriazole-1-yl-oxy-tris-pyrrolidino-phosphonium hexafluorophosphate, thionyl chloride, thionyl bromide, oxalyl chloride, cyanuric fluoride, isobutyl chloroformate, isopropenyl chloroformate, pentafluorophenyl trifluoroacetate, diphenylphoshoryl azide and diethylphosphoryl cyanide.

14. The process according to claim 1 wherein the organic base is selected from triethylamine, N,N-diisopropylethylamine, and pyridine.

15. The process according to claim 1 wherein the substituted hydroxylamine is reacted under Schotten-Baumen conditions.

16. The process according to claim 1 wherein the reducing agent is a hydride reagent.

17. The process according to claim 16 wherein the hydride reagent is selected from lithium aluminum hydride and diisobutyl aluminum hydride [DIBAL(H)].

18. The process according to claim 1, wherein the bicyclic heteroaryl carboxaldehydes of Formula I is 5,6-dihydro-4H-pyrrolo[1,2-b]pyrazole-2-carbaldehyde.

19. The process according to claim 1 wherein the bicyclic heteroaryl carboxaldehyde of Formula I is purified as the water soluble sodium bisulfite complex.

* * * * *